United States Patent [19]
Libbey et al.

[11] Patent Number: 5,324,252
[45] Date of Patent: * Jun. 28, 1994

[54] FOAM PADS USEFUL IN WOUND MANAGEMENT

[75] Inventors: Christopher J. Libbey, St. Joseph, Wis.; Lawrence R. Bramlage, Lexington, Ky.; Timothy C. Sandvig, Woodville, Wis.

[73] Assignee: Minnesota Mining and Manufacturing Company, St. Paul, Minn.

[*] Notice: The portion of the term of this patent subsequent to Apr. 20, 2010 has been disclaimed.

[21] Appl. No.: 980

[22] Filed: Jan. 6, 1993

Related U.S. Application Data

[60] Division of Ser. No. 800,571, Nov. 27, 1991, Pat. No. 5,203,764, which is a continuation-in-part of Ser. No. 674,565, Mar. 25, 1991, Pat. No. 5,195,945.

[51] Int. Cl.$^5$ ............................................. A61F 5/00
[52] U.S. Cl. ................................................ 602/5; 602/8
[58] Field of Search ............. 602/5, 6, 7, 8, 9, 11, 602/12, 20, 23, 43, 46, 60, 62, 27, 28; 521/172, 53, 137

[56] References Cited

U.S. PATENT DOCUMENTS

| | | | |
|---|---|---|---|
| 4,442,833 | 4/1984 | Dahlen | 602/8 |
| 4,672,956 | 6/1987 | Potter | 602/8 |
| 4,856,502 | 8/1989 | Ersfeld | 602/8 |
| 4,888,225 | 12/1989 | Sandvig | 602/8 |
| 4,893,617 | 1/1990 | Bartial | 602/8 |
| 4,934,356 | 6/1990 | Klintworth | 602/8 |
| 5,203,764 | 4/1993 | Libbey | 602/8 |

*Primary Examiner*—Michael A. Brown
*Attorney, Agent, or Firm*—Gary L. Griswold; Walter N. Kirn; Paul W. Busse

[57] ABSTRACT

The present invention relates to a method of dressing a wound using an open-celled foam pad prepared from a foam sheet impregnated with a water curable, isocyanate functional, polyurethane prepolymer resin. The pad can concurrently function as an orthotic pad. The pad exhibits the ability to wick wound exudate from the site of the wound, and also exhibits desirable conformability and comfort in use.

4 Claims, 1 Drawing Sheet

FOAM PADS USEFUL IN WOUND MANAGEMENT

This is a division of application Ser. No. 07/800,571 filed Nov. 27, 1991 now U.S. Pat. No. 5,203,764 issued Apr. 20, 1993 which is a continuation-in-part of Ser. No. 07/674,565, filed Mar. 25, 1991, now U.S. Pat. No. 5,195,945.

TECHNICAL FIELD

The present invention relates to the field of wound management and dressings, and in particular, to the use of foam dressings in wound management.

BACKGROUND ART

The field of orthotic pads, and materials useful therefore, is described in co-pending application Ser. No. 07/674,565.

The field of foam dressings in wound management is described, for instance, in S. Thomas, *Wound Management and Dressings*, The Pharmaceutical Press (1990) (see, for example, Chapter 5, "Foam Dressings", and references cited therein).

SUMMARY OF THE INVENTION

The present invention provides a foam pad useful for dressing a wound. The use of the foam pad as a wound dressing can be, and preferably is, in addition to its concurrent use as an orthotic pad, for instance, when the orthotic pad is in the form of a cast padding as described in co-pending U.S. application Ser. No. 07/674,565. In another aspect the present invention provides a wound management kit comprising a foam blank that can be cured by the user in order to prepare a foam pad, together with interface material(s), and overwrap means.

Surprisingly, it has been found that a foam pad of the present invention performs exceptionally well as a cast padding, not only for the reasons described in the above co-pending application, but also in situations in which there already exist open, exudate-producing incisions or wounds in the area covered by the cast. Additionally, comfort of the patient is improved, without the added weight and decreased permeability often seen over the course of using a conventional fiberglass cast lined with plaster. The foam pad appears to be able to substantially retain its porosity and to wick exudate away from the wound, thereby resulting in a much improved environment for healing the wound or incision.

The foam pad also appears to be able to better grip the skin of the patient, in comparison to a cotton padding, thereby improving the immobilization effect of cast. This results in reduced motion between the cast and limb, and thereby also appears to result in a reduction of pressure sores and sores due to cast movement. The use of the foam pad encourages the use of casts in situations, e.g., in veterinary use, where a marginal indication may be otherwise outweighed by the fear of pressure sore formation. In situations, for instance, of the prospective sale or show of an injured horse, the fear of complications from casting often discourages its use. In these instances, a cast with a foam pad of the present invention could be safely used with less fear of undue complications. This would be particularly true in the treatment of foals with injuries or deformities that would benefit from cast application.

As described more fully below, a foam pad that is used with a suitable casting material, e.g., a fiberglass casting tape, can cure to become an intimate part of the cast and therefore will neither be displaced or move within the cast after application. The foam pad is stable enough in its adherence to the cast tape that it also makes cast removal easier and safer, particularly for a cast that is closely applied to the limb. Since the foam pad is typically less rigid than a fiberglass cast material, the foam pad does not cut as readily with the cast saw as does the fiberglass cast material. This adds an additional layer of protection between the cast saw and the patient's skin. Cast removal can therefore be an easier and safer task than what is encountered after traditional cast application.

According to a presently preferred embodiment of the invention, a foam blank is provided which comprises a conformable, curable substrate. Preferably, the foam blank comprises an open-celled foam sheet impregnated with a water-curable, isocyanate functional, prepolymer resin. The foam pad is formed from the blank by activating the prepolymer resin, applying and conforming the blank to a part of the body, and holding the blank in place as it sets. When cured, the resultant foam pad bears an impression of the body part, i.e., it is closely and permanently conformed to the shape and position of the body part held in apposition to the blank during curing. The cured foam pad also exhibits both proper weight-bearing strength and cushioning properties, in order to support and/or cushion that body part, if desired.

The modulus of the cured foam pad, as defined below, can be determined and used as an indication of the ability of the pad to comfortably support weight, while the resilience, also defined below, can be determined as well, and used as an indication of the cushioning properties of the cured pad. Significantly, the resultant cured pad can exhibit "variable modulus and resilience", i.e., the modulus and resilience of portions of the resultant pad will vary according to the degree each portion was compressed as it cured. As a result, the ability of the cured pad to support and/or cushion the body part directly correlates with the needs of each portion of the opposing body part. The pad is most dense, and therefore has a higher modulus and is slightly more resilient, in areas where it was most compressed during curing. As a result, denser areas are better able to provide support, whereas less dense (lower modulus, slightly less resilient) areas are better able to provide a cushion effect.

Because the foam sheet itself, before impregnation with resin, is pliant and extensible, the conformability of the resin impregnated foam pad is quite good. Surprisingly, the foam sheet can be resin loaded to a very high degree and thereby impart the modulus and resilience desired in the cured foam pad. Also surprisingly, after resin loading the foam sheet to the extent necessary to achieve the desired properties, the resultant foam pad still exhibits variable modulus and resilience.

The foam sheets of the present invention can frequently be impregnated in a solvent-less manner, thereby avoiding any potential problem arising from prolonged contact of residual traces of solvent with the body part.

Good conformability, moldability and omnidirectional extensibility in applying the resin impregnated foam sheet are made possible with the present invention. As a result, good alignment of the cured foam pad with respect to the body part can be achieved. Another benefit of the present invention is that the surface of the resin impregnated foam pad is less tacky than would be expected, thereby greatly facilitating application of the pad. Furthermore, by the addition of catalysts as described herein, the blanks of the present inventions are able to be set and cured within a short period of time, yet with a low exotherm, thereby providing both convenience and comfort for the subject.

Foam pads of the present invention can be provided alone or in a kit, e.g., a kit that includes suitable interface material(s) and suitable overwrap means, such as casting tape or elastic bandage, as well as instructions for use and/or other suitable components such as medicaments.

These and other features of the present invention will become more fully apparent from the following description and appended claims.

DETAILED DESCRIPTION

Figure 1:
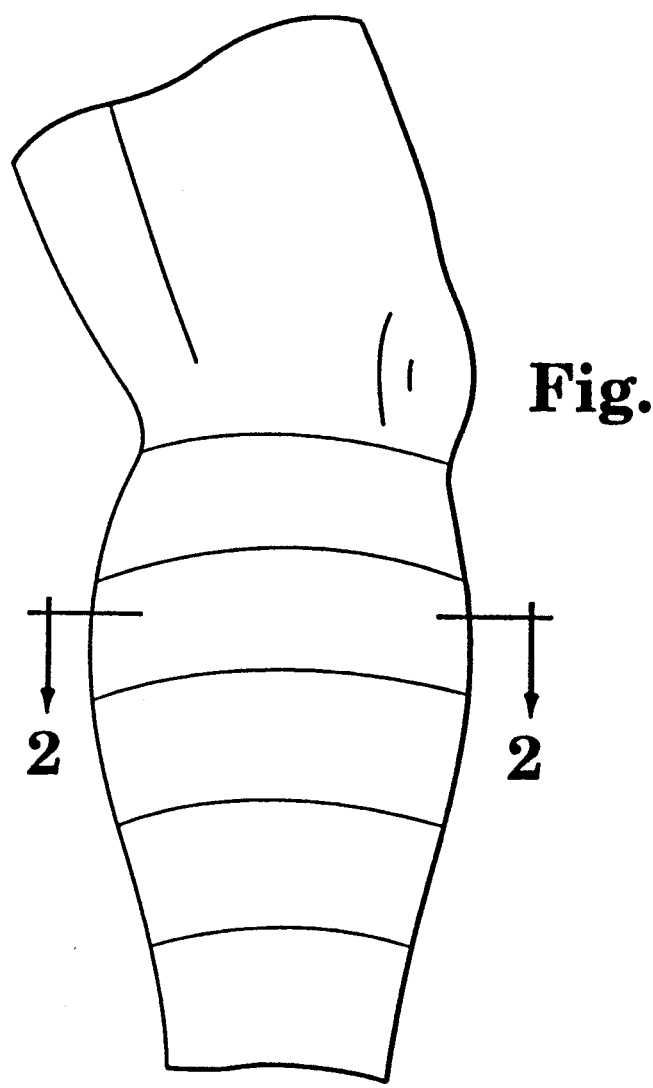
FIG. 1 is a perspective view of a resin impregnated foam pad of the invention wrapped around a patient's lower leg.
Figure 2:
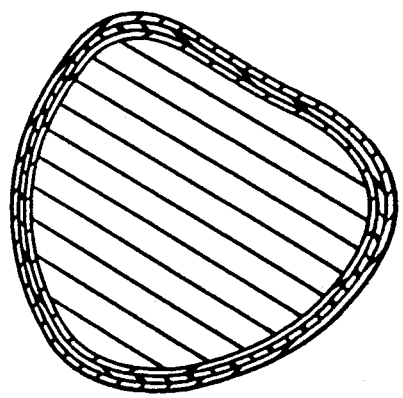
FIG. 2 is a cross sectional view taken along section line 2—2 of FIG. 1.

The subject matter of the present application is a continuation-in-part of the subject matter of the co-pending application cited above.

The subject matter of the co-pending application is directed to the use of the described foam pads as orthotic pads, and methods for forming such orthotic pads. The present invention provides that the materials described in the co-pending application are additionally and independently useful in wound management, i.e., as wound dressings. In some instances, the same foam pad will perform both functions, i.e., it will be used as an orthotic pad as previously described, and will concurrently serve as a wound dressing for wounds that exist in the area contacted by the pad. In other instances the foam pad will be used solely as a wound dressing, i.e., retained in contact with a wound, however not used to simultaneously cushion or support.

The present invention, in one aspect, provides a method of dressing a wound comprising the step of placing in fluid contact with the wound a foam pad prepared from a foam blank comprising an open-celled foam impregnated with a resin system, the resin system comprising a. a water curable prepolymer resin comprising an isocyanate component and a polyol component, said polyol component having an average hydroxyl equivalent weight greater than about 400 grams of polyol per hydroxyl group, and b. a catalyst capable of setting and curing said prepolymer resin upon exposure to water.

The word "wick" as used herein refers to the ability of the foam to transport liquids such as wound exudate from the area of the wound itself through the foam, e.g., to the surface of a compressing material such as a cast or bandage overwrap. The overwrap would typically be adjacent to the surface of the pad that is opposite to the surface contacting the wound. The word "contact" as used in the present application will be used interchangeably with the term "fluid contact", to mean that the pad is capable of wicking fluids from the wound site regardless of the presence of an interface material, such as a stockinette or gauze, between the pad and the wound. Generally, and preferably, pads of the present invention will be used with such an interface material. Any suitable interface material can be used that does not interfere with fluid contact between the wound site and the pad to the point where the foam pad would not serve its intended purpose.

The word "modulus" as used herein refers to the force required to produce a unit of deformation, e.g., compression, in a cured resin impregnated foam, i.e., modulus equals force/deformation. As such, it reflects the ability of the cured foam to comfortably support a body part, e.g., to provide proper weight-bearing strength for use in orthopedic applications. In turn, the "inverse of modulus" equals deformation/force. Thus, by using a constant force to compress different foams, one can measure and compare the percent deformation that each cured foam undergoes under that constant force.

The word "resilience", and inflected forms thereof, as used herein refers to the ability of a cured, resin impregnated foam that has been compressed, to recover substantially its original dimensions within a given period of time. As such, it reflects the ability of the cured foam to provide a cushioning effect, i.e., to recover its cured shape within a period of time after compression, e.g., during use, such as walking in the case of an orthotic footpad. As will become apparent to those skilled in the art, modulus and resilience are dependent in part on such factors as the nature and/or density of the foam, the nature and/or amount of resin impregnated in the foam, the weight and/or cured density of the final unitary blank, and the extent of compression of the foam during curing, i.e., its initial density compared to its cured density.

A blank of the present invention is generally comprised of a pliant, extensible foam sheet. The foam sheet is open-celled, and a curable resin is impregnated in the foam sheet. As used herein, the term "open-celled" refers to a foraminous structure having interconnecting or communicating orifices or cavities therein caused by a sufficient number of the wall membranes of the foam cells having been removed. Further, as used herein, the word "impregnated" and inflected forms thereof refers to the condition in which the resin is intermingled with and in surrounding relation to the wall membranes of the cells and the interconnected cells of the blank.

The foam sheet can comprise any one of a number of extensible foams that are open-celled, such as polyether- or polyester-based polyurethane foams. Importantly, the porosity of the blank must be such that it can be resin loaded sufficiently to provide a satisfactory pad. In this regard, the open-celled foam sheet preferably has from about 10 to about 50 pores per centimeter (i.e., about 30 to about 120 pores per inch). As used herein, the term "pores per centimeter" refers to the average number of pores located along a linear centimeter of the foam sheet. The number of pores per linear centimeter may be determined in a number of ways known to those skilled in the art, for example, by photomicrographic means, or by measuring the foam's resistance to air flow or a pressure differential, and using such information to calculate the approximate number of pores in the foam.

When the number of pores per centimeter is decreased below about 10, the foams become too coarse or rough, and typically do not hold enough resin to either provide the necessary strength for the resulting pad or to retain the desired conformation. Foam sheets having over about 50 pores per centimeter are not known to be presently commercially available. It will be understood, however, that the maximum number of pores per centimeter parameter is limited solely by the ability to load the foam with enough resin to provide sufficient properties for use as a wound dressing pad. Since foam sheets having over 50 pores per centimeter are not presently available commercially, it is difficult to predict the performance of foams having substantially more than 50 pores per centimeter, e.g., as to their resin loading characteristics and porosity. Preferably, the open-celled foam sheet used to form blank 10 has from about 20 to about 40 pores per centimeter.

The dimensions of the foam sheet depends in large part on the intended use of the pad. A blank of the present invention can be prepared and packaged having dimensions intended for use in apposition to a particular type and/or size of body part. Generally, the most important dimension will be the thickness of the blank, i.e., the distance(s) between the major surface to be contacted with the body part, and the opposite surface thereto. The other dimensions of the foam sheet, e.g., those that determine the surface area of the body part to be supported and/or cushioned can be varied as desired, as will become apparent to those skilled in the art. Uncured blanks or cured pads can generally be trimmed, as with a blade or scissors, or by grinding or abrading, respectively, to provide a desired size and shape.

Suitable blanks will typically be of a thickness between about 0.5 cm and about 5 cm, and preferably between about 1 cm and about 3 cm. The foam sheet need not be of uniform thickness either, particularly in situations, for example, where a portion of a body part requires additional support or cushioning. For use as a pad within an immobilizing device, such as a cast, the foam pad will typically be provided in the shape of a tape. The pad is sufficiently dimensioned to encompass the area of the body part to be covered.

Similarly, the resin impregnated foam sheet can be used alone or in combination with other materials, e.g., to vary its thickness, to provide additional strength, to provide a custom wear surface, to more widely vary its density and so forth. Such other materials can include, for instance, resin impregnated knit fabrics, or other resin impregnated foam sheet materials, e.g., utilizing a different foam and/or resin in order to provide such different properties. These other materials could also include such materials as plastics, leather, metal and the like and may be applied before, during or after setting or curing of the impregnated foam. Preferably, such other materials are of a type that will bond themselves to the orthotic blank as it cures, by virtue of the inherent adhesive qualities of the resin used in the blank.

The foam sheet utilized in the foam blank preferably has a density in the range of about 0.02 to about 0.15 g/cm$^3$, and most preferably, between about 0.02 and about 0.07 g/cm$^3$. Foam sheets possessing densities lower than about 0.02 g/cm$^3$ are not known to be presently commercially available. Foam sheets having densities higher than about 0.15 g/cm$^3$ tend to preclude the ability to resin load the foam to the extent necessary to achieve proper strength.

Examples of suitable foam sheets include "E-100", "E-290", "P-60", "P-80" and "P-100", each available from Illbruck U.S.A., Minneapolis, Minn. One presently preferred material for the foam sheet of the present invention is a polyether-based polyurethane foam sheet that is approximately 2 cm thick and is presently available from Illbruck USA, as type "E-150".

The most preferred resins for impregnating the foam sheet materials of the present invention are water-curable, isocyanate functional, polyurethane prepolymers prepared by the reaction of a polyol with an excess of a polyisocyanate. Suitable resins are disclosed, e.g., in U.S. Pat. Nos. 4,419,261 and 4,968,542, the disclosures of which are hereby incorporated by reference.

In order to obtain the desired modulus and resilience in a cured pad of the present invention, a significant factor in the choice of an appropriate polyol and an appropriate polyisocyanate to form the polyurethane prepolymer resin is the average hydroxyl equivalent weight, that is, the average molecular weight of the polyol(s) divided by the average number of reactive hydroxyl (OH) groups per mole of polyol(s). In general, the average hydroxyl equivalent weight of the polyol or polyol blend will be between about 400 grams and about 2400 grams, more preferably between about 1000 grams and about 2000 grams, and will preferably be greater than about 1000 grams when the isocyanate is polyaromatic, such as diphenylmethane diisocyanate.

Suitable polyols for use in the prepolymer resin include polyalkylene ethers derived from the condensation of alkylene oxides (such as those available from Union Carbide, South Charleston, W.Va., under the tradename "Niax" and from BASF Wyandotte Corp. under the tradename "Pluracol"), polytetramethylene ether glycols (such as the "Polymeg" polyols available from the Quaker Oats Co.), polycaprolactone polyols (such as the "Niax PCP" series of polyols available from Union Carbide), and polyester polyols (hydroxyl-terminated polyesters obtained from esterification of dicarboxylic acids and diols) such as the "Rucoflex" polyols available from Ruco division, Hooker Chemicals Co.

Examples of specific polyols that are useful include polypropylene glycols such as "PPG 2025" and "PPG 3025" available from Union Carbide, polypropylene triols such as "LHT 42" and "LHT 34", available from Union Carbide, and tetrols such as "Tetronic 1501" available from BASF Wyandotte Corp., Parsippany, N.J. Preferably all polyols used are urethane grade. The term "urethane grade" as used herein refers to polyols having a purity grade suitable for polyurethane production, as described, e.g., in Appendix B of *Polyurethanes—Chemistry and Technology*, J. H. Saunders and K. C. Frisch, eds., R. E. Krieger Publishing Co., Huntington, N.Y. (1978), the disclosure of which is hereby incorporated by reference.

However, it will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957) the disclosure of which is hereby incorporated by reference. Thus, for example, thiols and polyamines could also be used as "polyols" in the present invention and the term "polyols" will be considered to include such active hydrogen compounds. In such instances, the NCO:active hydrogen ratio of the polyisocyanate to the active hydrogen compound used to form the polythiocarbamate, polyurea, or other polymer, should fall within the same ranges as disclosed herein for the NCO:OH ratios.

Also in the present invention, the isocyanate equivalent weight of the prepolymer used is preferably relatively large. The isocyanate equivalent weight of the prepolymer is defined as the grams of prepolymer (i.e., polyol and isocyanate) per NCO group in the prepolymer. For purposes of the present invention, it has been found that the isocyanate equivalent weight should be within the range of about 400 grams to about 2300 grams of prepolymer per NCO group, and most preferably within the range of about 700 grams to about 1500 grams of prepolymer per NCO group.

Examples of isocyanates used to form polyisocyanates that are suitable for purposes of the present invention are disclosed, e.g., in U.S. Pat. Nos. 4,376,438, 4,433,680, and 4,502,479. Those isocyanates that are presently preferred include 2,4'-diphenylmethane diisocyanate, 4,4'-diphenylmethane diisocyanate, mixtures of these isomers together with possible small quantities of 2,2'-diphenylmethane diisocyanate (typical of commercially available diphenylmethane diisocyanates), and aromatic polyisocyanates and their mixtures, such as are derived from phosgenation of the condensation product of aniline and formaldehyde. It is presently preferred to use an isocyanate that has low volatility, such as diphenylmethane diisocyanate, rather than a more volatile material such as toluene diisocyanate. Commercially available isocyanate starting materials include "Isonatex ® 143L" available from Dow Chemical, LaPorte, Tex., which is a mixture of isocyanate compounds containing about 73% by weight of diphenylmethane diisocyanate; "Mondurx ® MRS-10" available from Mobay Chemical Corp., New Martinsville, W.Va.; and the polyaromatic polyisocyanate, "PAPI" available from Dow Chemical.

The NCO:OH ratio of the components of the prepolymer resin is preferably within the range of about 2:1 to about 8:1, and most preferably within the range of about 2.5:1 to about 4:1. It has been found that NCO:OH ratios lower than about 2:1 do not provide enough excess isocyanate groups to achieve adequate cross-linking of the resin during cure, while NCO:OH ratios greater than about 8:1 tend to produce undesirable stiffness. Higher NCO:OH ratios, i.e., approaching about 8:1, would generally be useful with polyols having higher hydroxyl equivalent weights.

Especially preferred resin components for use in the pads of the present invention are "Mondurx ® MRS-10" isocyanate and "LHT-34" polyol available from Union Carbide. Another preferred resin may be formed by reacting the "Isonatex ® 143L" isocyanate and the polypropylene oxide polyol available from Union Carbide as "LHT-42". To prolong the shelf life of blanks, it is preferred to include about 0.02 to about 0.1 percent (by weight based on the weight of the prepolymer resin) of benzoyl chloride and/or other suitable stabilizer (e.g., an antioxidant such as butylated hydroxy toluene at a level of about 0.05 to about 0.25 weight percent).

The term "resin system" as used herein refers to the prepolymer resin itself, i.e., the combination of polyol and isocyanate, as well as any other ingredients (e.g., catalyst(s), stabilizer(s), plasticizer(s), antioxidant(s), and the like) added to the prepolymer resin, or to either the polyol or isocyanate components thereof, prior to or simultaneously with their impregnation into the foam.

The resin systems of the present invention preferably contain a catalyst to control the set time and cure time of the resin. The term "set time" as used herein refers to the time needed for an activated blank to hold its conformed shape. At this time it could be removed from contact with the body part while it continues to cure. The term "cure time" as used herein refers to the time needed for the resin therein to cross-link to the furthest extent it is going to cross-link under the conditions chosen.

During the set time the activated blank should exhibit an exotherm compatible for use in apposition to a mammalian body part, e.g., preferably an exotherm of less than about 43° C. and more preferably about 40° C. The resin system of the present invention, as will become apparent to those skilled in the art, can be adjusted in a variety of ways to obtain suitable exotherm during cure, e.g., by decreasing the resin loading level; increasing the isocyanate equivalent weight of the prepolymer resin; reducing the NCO:OH ratio, and the like.

To produce suitable pads in accordance with the present invention, a set time of less than about 20 minutes following activation of the resin by exposure to water is preferred, with the most preferable set time being less than about 10 minutes. Frequently set times on the order of about 5 minutes or even about 4 minutes or about 3 minutes can be achieved. Suitable catalysts for moisture curing such prepolymer resins will become apparent to those skilled in the art. For example, tertiary amines such as 2,2'-dimorpholinodiethyl ether (DMDEE) described in U.S. Pat. No. 4,433,580, and 2,2'-dimorpholinyldialkyl ethers such as 4-[2-[1-methyl-2l-(4-morpholinyl)ethoxy]ethyl]morpholine (MEMPE) described in commonly assigned U.S. Pat. No. 4,705,840, in amounts ranging from about 0.5% to about 7% and preferably from about 2% to about 5% by weight, based on the weight of the prepolymer resin, may be used for this purpose.

Plasticizers can be, and preferably are, incorporated into the orthotic blank in order to maintain resilience of the cured orthotic pad over time, in a manner that will become apparent to those skilled in the art. For example, a plasticizer such as butyl benzylphthalate, available from Monsanto ("Santicizer 160") can be added to the resin system at between about 1% and about 20% by weight, based on the weight of the prepolymer resin. A preferred amount of this plasticizer is between about 8% and about 12% by weight. The use of a plasticizer is particularly preferred in order to prepare resins having NCO:OH ratios approaching about 8:1, in that resins having such higher ratios (e.g., greater than about 4:1) tend to be stiff when used without plasticizer.

Preferably, and particularly when the pad is to be used in apposition to the skin itself, the resin system used therein is impregnated into the foam sheet in a solvent-less manner, i.e., without the use of solvents such as organic solvents, e.g., methylene chloride, and the like. Generally, resins having a viscosity of about 100,000 centipoise or less can be impregnated into the foam sheets without the use of solvents by methods that will become apparent to those skilled in the art, e.g., by manually squeezing or otherwise manipulating the resin system into the foam.

Resin systems having higher viscosities, e.g., greater than about 100,000 cps can generally also be impregnated into foam sheets without the use of solvents, e.g., in the manner described in commonly assigned U.S. Pat. No. 4,946,726, wherein the polyol and isocyanate components of the prepolymer resin are blended immediately before impregnating into a foam sheet and allowed to react in situ in the foam sheet to form the prepolymer resin.

Preferably, the foam sheets of the present invention are impregnated with resin systems at coating weights of at least about 30% by weight of the total material, preferably at least about 40% by weight and particularly preferred are coating weights of at least about 50% by weight. Surprisingly, the prepolymer resin can often be impregnated into the foam sheets of the present invention so as to comprise as much as 80%, 90%, and even 95% by weight while still retaining suitable moduli, resilience and conformability, depending on the foam and on the resin chosen.

The resin impregnated foam sheets of the present invention are preferably prepared in a relatively low humidity chamber and sealed within a water vapor-impermeable package. This package is opened just prior to application of the blank.

Elements of the pads of the present invention and a presently preferred method by which pads can be formed and used as wound dressings will now be described.

A blank is preferably used by: 1) "activating" the prepolymer resin, i.e., exposing the blank to water to initiate setting and curing of the resin; 2) if necessary, manually squeezing out excess water; 3) properly positioning the pad on the patient, if necessary with the use of one or more appropriate interface materials; 4) keeping the pad in place as the resin sets, with sufficient pressure to cause the surface of the pad to become conformed to the shape of the patient's body part, and, if necessary; 5) trimming excess material from the cured pad in order to achieve the desired pad size or shape. The cured pad bears an impression of the body part, i.e., it conforms closely and permanently to the shape and position of the body parts held in apposition to the blank during curing. The cured pad also provides proper weight-bearing strength and cushioning properties for its intended use, and, depending upon the varying degrees to which each portion of the blank was compressed during curing, the resultant pad exhibits variable modulus and resilience.

Before actually applying a blank to a body part, a flexible stockinet or other suitable interface material is preferably placed between the subject's skin and the blank so as to prevent undesirable adhesion or contact between the blank and the body part. One or more interface materials can be used, e.g., a stockinette can be used to generally cover the overall area covered by the pad, together with a second interface material, such as a wound contact interface material that is specifically used to cover the area of an open wound.

Preferably the wound contact material is sufficiently porous to wound exudate to allow fluid contact to be established between the wound and the outerlying pad. More preferably, the wound contact interface material is of the type identified in Chapter 3, "Primary Wound Contact Materials" of the above-cited *Wound Management and Dressings*, S. Thomas, the entire disclosure of which is incorporated herein by reference. In particular, the materials identified by the heading as "Alternative Forms of Dressings with Low Adherence" (pp. 22-23) are desirable for use as interface materials in the present invention.

Such "non-adherent" wound contact interface materials are typically transparent and hypoallergenic, and provide two-way transport of gases and moisture, thereby allowing the wound to maintain a moist environment. Such materials are typically made from polymeric sheets, webs, or films. Examples of suitable non-adherent wound contact materials include Tegapore TM material (3M), Transite TM material (Smith & Nephew), and Telfa TM material (Kendall).

To expand further on the above description, a pad is formed by first activating the resin of the blank with water. This can be accomplished, for example, by exposing it to water, e.g, dipping it in water, spraying it with water, and so on. Next, the blank is preferably placed on or against the body part or another surface, e.g., a solid, flat surface, and aligned with the body part. In this regard, the resin impregnated foam has excellent compression moldability and conformability to provide a good fit to the shape of the body part.

The pad is retained compressed to the desired extent against the body part while the resin sets, optionally by the aid of overwrap means retaining the pad in place. The selection of suitable overwrap means can depend on the intended use of the foam pad. For instance, when the pad is to be used as a cast padding, the overwrap means can be the casting tape itself. When the pad is to be used in some other manner, e.g., solely as a wound dressing and not also as an orthotic pad, other suitable means can be used as an overwrap.

The term "overwrap means" as used herein refers to the means used to initially retain the pad in position as it cures, and/or the means used to retain the cured pad in position over the course of its subsequent use. These means can be the same or different. In the latter case, for instance, it might be desirable to use means that merely retain the pad in position with no compressive pressure, or with either less or more compressive pressure than might have initially been used to cure the pad. When the pad is applied to a limb, for instance, such means could include anything from a circumferential, overlapped, wrapping of the pad and limb with an elastic bandage, to the use of a piece of standard surgical tape that extends sufficiently beyond the edges of the pad to retain the pad in position on the skin.

It will be understood that various modifications and changes may be made by those skilled in the art to accommodate different situations.

The present invention will be further understood in view of the following Examples which are merely illustrative and are not to be considered as comprehensive or limiting in any way. Examples 1-14 will be repeated from co-pending U.S. application Ser. No. 07/674,565 in order to provide relevant information regarding the taking and evaluation of materials useful in the present invention.

EXAMPLE 1

In this Example, an orthotic footpad within the scope of the present invention was prepared. First, a polyether-based polyurethane foam, having a thickness of approximately 1.95 cm was obtained from Illbruck U.S.A. (Minneapolis, Minn.) as type "E-100". This foam material has a density of about 0.02 g/cm$^2$ and a pore size of about 24 pores per linear centimeter. A 10.2 cm by 30.5 cm sheet of this foam material was cut out with a scissors. The weight of the foam sheet was determined to be about 12 grams, and this figure was used to determine the correct amount, in grams, of the resin system to be used in order to achieve a resin loading of about 85% by weight of the final resin impregnated foam sheet.

A polyurethane prepolymer resin having an NCO:OH ratio of about 3.0:1 was prepared as follows. In an atmosphere maintained at about 4% relative humidity, a vessel was charged with 396 grams of isocyanate ("Mondurx ® MRS-10," obtained from Mobay Chemical). (This isocyanate compound has an NCO equivalent weight of about 132 grams of isocyanate per NCO group.) A second vessel was charged with 1650 grams of "LHT-34" as the polyol, which was obtained from Union Carbide. (The LHT-34 had an OH equivalent weight of about 1650 grams of polyol per OH group.) To the LHT-34 in the second vessel was added 0.4 grams of benzoyl chloride as stabilizer, 236 grams of butyl benzylphthalate ("BBPTH", Monsanto) as plasticizer, and 85 grams of 4-[2-[1-methyl-2-(4-morpholinyl)ethoxy]ethyl]morpholine ("MEMPE") as catalyst, prepared as described in Example 1 of commonly assigned U.S. Pat. No. 4,705,840, the disclosure of which is hereby incorporated by reference. The mixture in the second vessel was then added to the isocyanate compound contained in the first vessel, and the components were blended together. (This prepolymer mixture had an NCO equivalent weight of about 1023 grams of prepolymer resin per NCO group.) Immediately after blending these components together, the blended resin system was impregnated into the foam sheet in an amount such that the resin system represented about 85% by weight of the final product. Such impregnation of the resin system into the foam sheet was achieved in a moisture-free chamber by spreading the resin system over all surfaces of the foam sheet and then manually kneading the resin system into the foam material. The viscosity of the resin system 24 hours after blending the components (to allow sufficient time for reaction to occur) was determined to be about 20,000 centipoise, using a Brookfield viscometer, Model RV, Brookfield Engineering Laboratories, Stoughton, Mass. The blank thus prepared was then sealed in an air-tight pouch to protect the blank from exposure to moisture.

Later, the blank prepared in this Example 1 was applied to a foot by the following procedure. The impregnated foam blank was removed from the pouch, and activated by dipping in room temperature water. Excess water was removed by squeezing. The activated, impregnated foam blank was covered with a 0.038 mm (1.5 mil) thick film of Elastoflex "P", available from Clopay Co. A subject's bare foot was then settled into the foam blank causing the foam to conform in shape to the heel, sole and lower sides of the foot. Care was taken not to completely compress the foam under the heel or ball of the subject's foot.

After being held in place for about five minutes, the foot was removed from the foam blank leaving an exact impression of the subject's foot. The Elastoflex "P" film was peeled off and when cured, the orthotic pad was trimmed as necessary with a scissors and hand held grinder (Dremel "Moto Tool", Sears Roebuck) to fit the subject's shoe as an insert. The finished insert conformed exactly to the subject's foot, provided excellent support and cushioning, particularly in the arch area, and was comfortable to wear.

EXAMPLE 2

In this example, an orthotic shinpad within the scope of the present invention was prepared according to the procedure of Example 1 with the following exceptions. In this Example 2, a polyurethane prepolymer resin having an NCO:OH ratio of about 2.5:1 was prepared by charging the first vessel with 360 grams of isocyanate ("Isonatex® 143L", obtained from Upjohn and having an NCO equivalent weight of about 144 grams of isocyanate per NCO group). The second vessel was charged with 1335 grams of polyol ("LHT-42", obtained from Union Carbide), and 0.17 grams of benzoyl chloride as stabilizer, 188 grams of BBPTH as plasticizer, and 67 grams of MEMPE as catalyst. In this example, the resin system, i.e., the prepolymer resin itself as well as the stabilizer, plasticizer and catalyst represented about 80% by weight of the final product, and the prepolymer resin had an NCO equivalent weight of about 1130 grams of prepolymer resin per NCO group. The blended resin system had a measured viscosity of approximately 22,000 centipoise. A stockinette was placed over a subject's lower leg. The water activated, impregnated foam blank was positioned against the stockinette and over the shin area. Using a stretch bandage overwrap, the impregnated foam blank was partially compressed and conformed to the shin as it cured. The temperature that would be felt by the patient during curing was determined to be less than about 39° C., using a thermometer placed under the blank as it cured. The orthotic shinpad formed in this example was sufficiently set after about 5 minutes from the initial activation of the prepolymer resin. The cured shinpad was trimmed to remove any excess material. The finished pad was soft and resilient and retained the exact shape of the subject's shin. When held in place with an elastic bandage or stockinette the pad offered excellent protection for the shin.

EXAMPLES 3-14

The inverse modulus and resilience of a variety of pads of the present invention were compared by the following means, using force and time values that roughly approximate the forces and times an orthotic footpad would be expected to be subjected to in the course of a subject walking.

The inverse modulus values given below represent the observed percent (%) deformation of each cured pad in response to a load of 1.05 kg/cm$^3$ (15 psi) applied over a period of 0.5 seconds.

Resilience was calculated as the percent of its original dimensions a cured pad recovers within 0.5 seconds, after being deformed (compressed) to one-half of its cured thickness.

Both inverse modulus and resilience were calculated for orthotic pads cured at both 0 and 50% compression, i.e., cured at both their original, uncompressed, thickness, and cured at a 50% compressed thickness.

The experimental method used to calculate modulus and resilience was as follows:

Cyclic stress-strain experiments were performed using an MTS 810 Material Test System (MTS Systems Corp., Minneapolis, Minn.). All experiments were performed at a frequency of 1 Hertz in a haversine displacement mode as controlled by the 410 Digital Function Generator. The 442 Controller was adjusted so that actuator displacement and load cell output corresponded to 1.27 cm/volt (0.5 inch/volt) and 13.6 kg/volt (30 pounds-force/volt), respectively. All loads were measured using an MTS Model 661.21A-01 Load Cell. Actuator linear variable displacement transducer "LVDT" and load cell voltages were recorded by a Nicolet 4094 Digital Oscilloscope. (Nicolet Instruments, Madison, Wis.)

A 10.16 cm (4 inch) diameter, 2.54 cm (1 inch) thick steel disc test fixture was attached to the MTS load cell. A 15.24 cm (6 inch) diameter, 2.54 cm (1 inch) thick steel disc test fixture was attached to the MTS actuator. As employed for testing, the load cell and actuator discs were coaxially aligned and the faces of each disc were parallel to each other. The test specimen was sandwiched between these two discs as tested. Movement of the actuator disc toward the load cell disc would result in sample compression and produce a force on the load cell disc.

Tested samples measured approximately 12.7 cm×15.24 cm (5 inch×6 inch). In all cases samples were sufficiently wide enough to completely cover the face of the load cell disc. The tested samples were 1.65 to 2.16 cm (0.65 to 0.85 inch) thick for the uncompressed-cured samples and 0.83 to 1.08 cm for the 50% compressed-cured samples.

To obtain the inverse modulus (% deformation) values, the MTS system was used in the load control mode where a continuous sinusoidal loading was maintained on the load cell and the necessary actuator displacement needed to maintain the programmed load was monitored. The sample to be measured was first placed between the test fixture discs and the actuator was positioned so that the preload force on the sample was 16.8 g/cm$^2$ (0.24 psi) (corresponding to a load cell voltage output of 0.10 volt). The 442 Controller was adjusted so that this position corresponded to an actuator LVDT output of zero volts. During the experiment, the actuator position was adjusted by the 442 Controller so that the force on the load cell varied sinusoidally between 1.36 and 85.7 kg (3.0 and 188.5 pounds-force) corresponding to a sample loading of 0.0168 and 1.055 kg/cm$^2$ (0.24 and 15.0 psi), respectively. The voltages corresponding to the position of the actuator and the force on the load cell were monitored by the Nicolet 4094 Digital Oscilloscope. The stress-strain hysteresis loop was monitored until no changes due to sample relaxation were observed. Four consecutive hysteresis loops were then stored in the oscilloscope pending analysis.

A variety of orthotic pads were prepared and their inverse moduli and resilience calculated according to the above procedures, the results of which are listed below in TABLE I.

Resins were prepared as described in Example 2, using Isonate ® 143L as the isocyanate, and a final concentration in the resin system of 0.07% benzoyl chloride (as stabilizer), 4.0% MEMPE (as catalyst) and 0.2% butylated hydroxytoluene (as stabilizer). None of the samples contained plasticizer. As the polyol, Examples 3-8 were prepared in pairs using triols of varying OH equivalent weights (1650, 2000 and 1350, respectively) and Examples 9-14 were prepared in pairs using diols of varying OH equivalent weights (1500, 500 and 1000, respectively). The odd-numbered Examples of each pair were prepared at an NCO:OH ratio of 2.5:1, and the even numbered at 3:1.

The orthotic pads were each prepared using 1.9 cm (¾ inch) thick foam ("E-150") impregnated at an 85% resin system coating weight. The OH equivalent weight of the polyols used was varied as shown in TABLE I. Also listed in TABLE I are the subjective determination ("comments") of the suitability of each pad for use as an orthotic pad.

TABLE

| Ex. | polyol(OH eq. wt) | Inverse Modulus (% deformation) | | Resilience (% recovery) | | Comments |
| --- | --- | --- | --- | --- | --- | --- |
| | | Uncomp. | 50% Comp. | Uncomp. | 50% Comp. | |
| 3 | 1650 triols | 80 | 53 | 45 | 87 | Excellent |
| 4 | 1650 triols | 76 | 42 | 51 | 91 | " |
| 5 | 2000 triols | 80 | 57 | 40 | 82 | " |
| 6 | 2000 triols | 78 | 47 | 46 | 90 | " |
| 7 | 1350 triols | 77 | 42 | 51 | 92 | " |
| 8 | 1350 triols | 78 | 44 | 49 | 91 | " |
| 9 | 1500 diols | 80 | 47 | 30 | 81 | Useful |
| 10 | 1500 diols | 80 | 50 | 35 | 78 | " |
| 11 | 500 diols | 77 | 38 | 32 | 71 | Stiff |
| 12 | 500 diols | 63 | 23 | 40 | 73 | " |
| 13 | 1000 diols | 78 | 45 | 39 | 86 | Useful |
| 14 | 1000 diols | 79 | 47 | 38 | 81 | " | relaxation were observed. Four consecutive hysteresis loops were then stored in he oscilloscope pending analysis.

To obtain the resilience (% recovery) values, the MTS system was used in the stroke control mode where a continuous sinusoidal displacement of fixed amplitude was applied to the actuator and the resulting force on the load cell was monitored. The sample to be measured was first placed between the test fixture discs and the actuator disc was positioned so that the preload force on the sample was 16.8 g/cm$^2$ (0.24 psi) (corresponding to a load cell voltage output of 0.10 volt). The 442 Controller was adjusted so that this position corresponded to an actuator LVDT output of zero volts. The distance between the disc faces was measured and the 442 Controller was adjusted so that the maximum displacement of the actuator during the test would be exactly one-half of the disc face distance. During the experiment, the actuator cycled sinusoidally between its zero position and a point at which the disc face separation was 50% of the initial separation. The voltages corresponding to the position of the actuator and the force on the load cell were monitored by the Nicolet 4094 Digital Oscilloscope. The stress-strain hysteresis loop was monitored until no changes due to sample relaxation were observed. Four consecutive hysteresis loops were then stored in the oscilloscope pending analysis.

As seen in TABLE I, preferable orthotic pads prepared as described in Examples 3-14 exhibit inverse moduli (in the uncompressed and 50% compressed states) of between about 40% and about 100% deformation, and preferably between about 45% and about 90% deformation, in response to a load of 1.05 kg/cm$^2$ applied over a period of 0.5 seconds. Correspondingly, preferable orthotic pads prepared as described in these Examples exhibit resilience (in the uncompressed and 50% compressed states) of between about 30% and about 100% recovery, and preferably between about 40% and about 100% recovery, within 0.5 seconds, after being deformed to one-half their cured thickness. Generally, suitable orthotic pads of the present invention will recover essentially all of their original shape within a reasonable period of time for use, e.g., within seconds of their being deformed.

EXAMPLE 15

A resin impregnated open-celled foam was prepared in the following manner. The following resin system was impregnated into an open-celled foam ("P-100 Foam", ⅛ inch×3 inch×8 feet (3.2 mm×76.2 mm×2.4 m), obtained from Technifoam Inc.) to a coating weight of 86%:

| | |
|---|---|
| Isonate TM 143L isocyanate | 21% |
| Butyl benzylphthalate | 10% |
| MEMPE | 1.5% |
| Benzoyl chloride | 0.06% |
| LHT-42 TM polyol | 61.64% |
| Pluronic F-38 (A polyethylene oxide-terminated polypropylene oxide, BASF Corp.) | 4% |
| DB-100 TM (A silicone oil - used as an antifoaming agent, Dow Corning) | 0.2% |
| Ionol TM (butylated hydroxytoluene) | 0.33% |
| "Reactint Yellow" (A yellow dye, Milliken Chemicals) | 0.25% |
| Cab-o-sil TM (Hydrophobic fumed silica, Cabot) | 1% |
| TOTAL | 100% |

Coating was performed under dryroom conditions and the resin impregnated foam was rolled and placed in a moisture proof pouch for storage. The Pluronic TM F-38 component was used to provide a non-tacky, or "slippery" feel to the surface of the impregnated foam upon water activation, in order to improve the user's abiltity to handle the foam in the course of unrolling and applying the roll. The Cab-o-sil TM silica was included as a thixotrope to increase the viscosity of the resin, thereby limiting resin migration within and/or from the foam.

Rolls of the resin impregnated foam were used as cast padding for equine limbs. The foam cast padding was applied to 40 clinical cases for evaluation of pressure sore prevention and compatibility of the resin with the skin of the equine limb for both short and long term use. Casts were applied for a variety of time periods, depending on the clinical situation. They were applied mostly for immobilization of orthopedic injuries, however, they were also used for treatment of flexural and angular limb deformities in foals as well as in the treatment of chronic laminitis. In this latter application, the resin impregnated foam was used for the protection of the sole surface of the foot.

Other materials used were synthetic stockinette, ⅛ inch×3/8 inch (3.2 mm×76.2 mm) cast felt, and conventional fiberglass casting tape (Vetcast TM Plus Casting Tape, 3M). The resin impregnated foam was applied as a thin layer to be used under the cast material and directly over synthetic stockinette covering the limb. No additional padding was used with the exception of felt used to form a collar at the top of the cast. The foam was applied in a spiral application with a one-half width overlap starting proximally and spiraling down the limb. The overlap created a double layer of foam resulting in ¼ inch (6.4 mm) of foam being present over the entire limb from the carpus or tarsus to the coronary band. A third layer of foam over the fetlock or over an incision was used in some instances. The foam material was then overlaid with the fiberglass cast material applied in a conventional manner. The cured cast material was left on the limb as appropriate for the clinical condition being treated, then removed by conventional means.

The fiberglass casting tape bonded tightly to the resin impregnated foam, with the foam essentially becoming part of the inner surface of the cast. The foam also bonded well to itself, i.e., at points of contact where overlapped, creating a single unit, the layers of which were visually indistinguishable. The resin impregnated foam conformed well to the anatomy of the limb. It compressed more at the bony prominences, such as over the sesamoids and it expanded into depressions on the surface of the limb, such as between the flexor tendons and the suspensory ligament. This conformation of the cast to the limb virtually eliminated problems with pressure sores in the area of the sesamoid and at the heels of the foot, two places which are commonly trouble spots for pressure sores during clinical casting application.

In addition, the foam-lined cast maintained closer contact with a greater surface area of the limb than would ordinarily be seen with conventional fiberglass casts. This contact improved the ability to closely adapt external cast immobilization to the limb for use in situations such as a fracture of the metacarpus. The foam created a comfortable " grip" on the limb without uneven application of pressure to the bony prominences. Therefore, a more rigid adaptation of the cast for a more rigid immobilization of the limb was the result. Casts could be applied more closely to the limb, thereby reducing the need for additional underlying padding, and increasing the cast's ability to limit motion between the limb and the cast and between segments of the limb.

Pressure sores were occasionally encountered at the proximal end of the cast in the area where the dorsal aspect of the cannon bone would press tightly against the cast if ideal standing conformation of the cast was not attained. These pressure sores, however were primarily the result of misalignment of the limb and cast to the ground surface. They resulted from pressure of the cast material onto the vulnerable skin at the edge of the cast as the horse stood on the limb.

Surprisingly, in situations where incisions or wounds were present on the limb prior to cast application, the foam appeared to absorb exudate and wick it away from such incisions or wounds, thereby allowing the exudate to percolate through to the exterior of the cast much better than would be expected from traditional cotton cast padding. Wounds appeared to be both cleaner and dryer after removal of the cast than would be the case with conventional casting techniques involving cotton cast padding.

EXAMPLE 16

A patient's leg ulcer, located in the lower calf area of a human leg is cleaned, debrided, and medicated as the attending physician deems necessary.

The ulcerated area is covered by interface material(s) selected from one or more of the following:
 a clean stockinette
 a wound dressing, such as sterile gauze
 non-adherent wound contact material (e.g., Tegapore TM material, 3M)

A roll of resin impregnated foam padding prepared as described in EXAMPLE 15 is removed from its moisture proof pouch and activated by dipping in water. Water is pumped through the foam roll by squeezing. The activated, impregnated foam is wrapped over the ulcerated area, overlapping each wrap by approximately half. The activated, impregnated foam is followed by wrapping with an ACE ™ bandage that compresses the foam to approximately one-half of its initial thickness. The activated, impregnated foam cures in about 4 minutes, bonding the overlapping layers of foam and the stockinette into a single unit.

The cured dressing closely replicates the shape and contours of the limb and exhibits variable modulus and resilience. The porous nature of the cured dressing, together with the precise fit, serve to wick excess exudate away from the ulcer while maintaining a moist healing environment. The cured resin impregnated foam, in combination with compression wraps and interface material(s), provides improved compression for the management of venous ulcerations, providing the opportunity for improved healing. Additionally, the cured foam can be removed from the limb and reapplied with fresh interface materials.

We claim:

1. A foam pad comprising an open-celled foam impregnated with a resin system, said resin system comprising
    a. a water curable prepolymer resin comprising an isocyanate component and a polyol component, said polyol component having an average hydroxyl equivalent weight greater than about 400 grams of polyol per hydroxyl group, and
    b. a catalyst capable of setting and curing said prepolymer resin upon exposure to water,
wherein said pad is a wound dressing in fluid contact with a wound.

2. The foam pad of claim 1 wherein the foam pad closely replicates the shape and contours of a patient's body surrounding the wound and wicks away exudate from the wound.

3. The foam pad of claim 2 wherein the wound is on the patient's limb.

4. The foam pad of claim 1 wherein the foam pad closely replicates the shape and contours of the a patient's body surrounding the wound and is compressed against the body and wound without forming pressure sores.

* * * * *

UNITED STATES PATENT AND TRADEMARK OFFICE
CERTIFICATE OF CORRECTION

PATENT NO. : 5,324,252
DATED : June 28, 1994
INVENTOR(S) : Christopher J. Libbey, Timothy C. Sandvig, Larry R. Bramlage It is certified that error appears in the above-indentified patent and that said Letters Patent is hereby corrected as shown below:

| | |
|---|---|
| Col. 7, line 43 | "Mondurx®" should read --Mondur®-- |
| Col. 7, line 46 | "Isonatex®" should read --Isonate®-- |
| Col. 8, lines 24-25 | "4-[2-[1-methyl-21-(4-morpholinyl)ethoxy]ethyl]morpholine" should read --4-[2-[1-methyl-2-(4-morpholinyl)-ethoxy]ethyl]morpholine-- |
| Col. 10, line 45 | "taking" should read --making-- |
| Col. 10, line 54 | "0.02 g/cm$^2$" should read --0.02 g/cm$^3$-- |
| Col. 12, line 35 | "1.05 kg/cm$^3$" should read --1.05 kg/cm$^2$-- |

Signed and Sealed this

Eleventh Day of April, 1995

*Attest:*

BRUCE LEHMAN

*Attesting Officer*   Commissioner of Patents and Trademarks